US010126367B2

(12) United States Patent
Lee et al.

(10) Patent No.: US 10,126,367 B2
(45) Date of Patent: Nov. 13, 2018

(54) DETECTION METHOD OF LI PLATING, METHOD AND APPARATUS FOR CHARGING SECONDARY BATTERY AND SECONDARY BATTERY SYSTEM USING THE SAME

(71) Applicant: LG CHEM, LTD., Seoul (KR)

(72) Inventors: Hyeok-Moo Lee, Daejeon (KR);
Hyo-Mi Kim, Daejeon (KR);
Song-Taek Oh, Daejeon (KR); Sol-Nip Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 34 days.

(21) Appl. No.: 15/310,193

(22) PCT Filed: Jun. 20, 2016

(86) PCT No.: PCT/KR2016/006532
§ 371 (c)(1),
(2) Date: Nov. 10, 2016

(87) PCT Pub. No.: WO2017/034135
PCT Pub. Date: Mar. 2, 2017

(65) Prior Publication Data
US 2017/0234930 A1 Aug. 17, 2017

(30) Foreign Application Priority Data
Aug. 24, 2015 (KR) .................. 10-2015-0118919

(51) Int. Cl.
*H02J 7/00* (2006.01)
*G01R 31/36* (2006.01)
(Continued)

(52) U.S. Cl.
CPC ......... *G01R 31/3624* (2013.01); *G01N 27/02* (2013.01); *G01R 31/36* (2013.01);
(Continued)

(58) Field of Classification Search
CPC .............. G01R 31/3624; G01R 31/362; G01R 31/3606; G01R 31/3634; G01R 31/3637;
(Continued)

(56) References Cited

U.S. PATENT DOCUMENTS

2006/0093894 A1* 5/2006 Scott .................... A61N 1/3787
429/50
2011/0012604 A1* 1/2011 Tsujiko ................. H01M 10/48
324/427

(Continued)

FOREIGN PATENT DOCUMENTS

JP   2011-171213 A   9/2011
JP   2011-220917 A   11/2011
(Continued)

OTHER PUBLICATIONS

Rosso M et al: "Onset of dendritic growth in lithium/polymer cells", Journal of Power Sources, Elsevier SA, CH, vol. 97, Jan. 22, 2001 (Jan. 22, 2001), pp. 804-806.

*Primary Examiner* — Nathaniel Pelton
(74) *Attorney, Agent, or Firm* — Birch, Stewart, Kolasch & Birch, LLP (57) ABSTRACT

Provided is a non-destructive method for detecting lithium plating by which lithium plating can be detected in real time in an actual use environment of a secondary battery, a secondary battery charging method and apparatus for charging a secondary battery under the condition in which lithium plating does not occur by using this method, and a secondary battery system for detecting the state of a secondary battery by using this method. The method for detecting lithium plating according to the present disclosure is a method which detects lithium plating in a negative electrode in real time by observing a change in battery voltage as a function of SOC during charging a secondary battery, and determines a point at which a rise speed of the battery voltage slows down as a lithium plating occurrence point.

12 Claims, 9 Drawing Sheets

(51) Int. Cl.
  *G01N 27/02*    (2006.01)
  *H01M 10/44*    (2006.01)
  *H01M 10/0525*  (2010.01)
  *H01M 10/48*    (2006.01)
  *G01R 31/44*    (2006.01)

(52) U.S. Cl.
  CPC ........ *G01R 31/44* (2013.01); *H01M 10/0525* (2013.01); *H01M 10/44* (2013.01); *H01M 10/48* (2013.01); *H02J 7/0052* (2013.01)

(58) Field of Classification Search
  CPC .......... G01R 31/3679; H01M 10/0525; H01M 10/44; H01M 10/48; H02J 7/0052
  USPC ........................................................ 320/162
  See application file for complete search history.

(56)         References Cited

U.S. PATENT DOCUMENTS

| | | |
|---|---|---|
| 2011/0206952 A1 | 8/2011 | Mano et al. |
| 2011/0298417 A1* | 12/2011 | Stewart ................ G01R 31/025 320/107 |
| 2012/0179398 A1 | 7/2012 | Ueki et al. |
| 2012/0226455 A1 | 9/2012 | Kumashiro et al. |
| 2013/0069584 A1* | 3/2013 | Nagakura ............. H02J 7/0086 320/107 |
| 2013/0099794 A1 | 4/2013 | Takahashi et al. |
| 2013/0314050 A1* | 11/2013 | Matsubara ................ H02J 7/00 320/134 |
| 2014/0266060 A1* | 9/2014 | Ying .................... G01R 31/361 320/134 |
| 2015/0147597 A1* | 5/2015 | Otomo .................. H01M 4/134 429/7 |
| 2016/0061908 A1* | 3/2016 | Torai .................. G01R 31/3606 702/63 |

FOREIGN PATENT DOCUMENTS

| | | |
|---|---|---|
| JP | 2012-49040 A | 9/2012 |
| JP | 2013-196805 A | 9/2013 |
| JP | 2015-104138 A | 6/2015 |
| KR | 10-2012-0099583 A | 9/2012 |
| KR | 10-2013-0031858 A | 3/2013 |
| WO | WO 2011/039882 A1 | 4/2011 |

* cited by examiner

FIG. 9

DETECTION METHOD OF LI PLATING, METHOD AND APPARATUS FOR CHARGING SECONDARY BATTERY AND SECONDARY BATTERY SYSTEM USING THE SAME

TECHNICAL FIELD

The present disclosure relates to a method for detecting lithium plating in a lithium ion secondary battery, and more particularly, to a method for determining whether lithium plating occurred in real time by a non-destructive method. Further, the present disclosure relates to a charging method and apparatus for charging a secondary battery under the condition in which lithium plating does not occur by using this method. In addition, the present disclosure relates to a secondary battery system for detecting the state of a secondary battery by using this method. The present application claims priority to Korean Patent Application No. 10-2015-0118919 filed in the Republic of Korea on Aug. 24, 2015, the disclosures of which are incorporated herein by reference.

BACKGROUND ART

Recently, with the dramatic increasing demand for handheld electronic products such as laptop computers and mobile phones and the growing demand for electric carts, electric wheelchairs, and electric bikes, studies are being intensively made on high performance secondary battery that can be recharged repeatedly. Also, more recently, with the gradual exhaustion of carbon energy and the increasing interest in environment, the global demand for hybrid electric vehicle (HEV) and electric vehicle (EV) is gradually increasing. Accordingly, deeper interest and more intensive studies concentrate on secondary batteries for vehicle as a key component of HEV or EV.

Lithium ion secondary batteries are the most realistic technology for high performance secondary batteries and secondary batteries for vehicle. A lithium ion secondary battery works by repeated intercalation and deintercalation of lithium ions at a negative electrode and a positive electrode. A lithium salt containing electrolyte in which lithium ions move but electrons do not move is present between the electrodes.

Many studies are being made on secondary batteries in aspects of high capacity and high density, but it is also important to improve life and safety. To this end, it is necessary to inhibit a decomposition reaction with an electrolyte solution on the electrode surface, and prevent overcharge/overdischarge.

Particularly, there is a need to prevent the deposition of lithium, so-called lithium-plating (Li-plating), on the negative electrode surface. The reason is that lithium plating not only causes side reactions with an electrolyte solution and changes in kinetic balance of the secondary battery, resulting in degradation of the secondary battery such as capacity loss, but also affects the life of the secondary battery and causes a safety problem with loss of an overcharge control function.

Conventionally, however, it is very difficult to detect lithium plating in secondary batteries in real time. Earlier non-destructive detection of lithium plating on the negative electrode includes discharging at low temperature, heat capacity analysis, and thickness increase analysis. However, they do not involve measuring in an environment in which a secondary battery is used. Therefore, there is a need for real-time detection of lithium plating in an actual use environment of a secondary battery.

DISCLOSURE

Technical Problem

The present disclosure is directed to providing a nondestructive method for detecting lithium plating by which lithium plating can be detected in real time in an actual use environment of a secondary battery.

The present disclosure is further directed to providing a secondary battery charging method and apparatus for charging a secondary battery under the condition in which lithium plating does not occur by using this method.

The present disclosure is further directed to providing a secondary battery system for detecting the state of a secondary battery by using this method.

Technical Solution

To achieve the object, a method for detecting lithium plating according to the present disclosure is a method for detecting lithium plating in a negative electrode in real time by observing a change in battery voltage (full cell potential) as a function of SOC during charging a secondary battery, and determines a point at which a rise speed of the battery voltage slows down as a lithium plating occurrence point.

In an embodiment, a SOC-V graph is obtained by measuring battery voltage as a function of SOC while charging the secondary battery. From this, a SOC-dV/dQ graph showing a change in battery voltage dV/dQ as a function of SOC is obtained. A point at which a slope increase slows down on the SOC-dV/dQ graph is determined as the lithium plating occurrence point.

To achieve another object, a method for charging a secondary battery according to the present disclosure includes acquiring data by measuring battery voltage (full cell potential) as a function of SOC at different charge rates; obtaining a protocol designed to change a charge rate stepwise by setting a point at which a rise speed of the battery voltage slows down as a lithium plating occurrence point and charging limitation from the acquired data; and charging a secondary battery according to the protocol.

The charge rate at the data acquisition step may be in a range of 0.25 C~5 C.

The protocol may have an initial charge rate higher than 1 C. Particularly, the protocol may have an initial charge rate of from 1.5 C to 5 C. The protocol may include a stepwise-decreasing charge rate and charge voltage information after termination of charging at each charge rate.

An apparatus for charging a secondary battery according to the present disclosure includes a power source unit configured to output charge voltage inputted from a commercial power source; and a charging unit configured to output the charge voltage inputted from the power source unit to a secondary battery as a charge current, to charge the secondary battery, and when battery voltage (full cell potential) of the secondary battery reaches a preset stage, to take control of the charge current to cause the charge current outputted to the secondary battery to change stepwise, wherein the charging unit charges the secondary battery with the stepwise-adjusted charge current according to a protocol designed to change a charge rate stepwise by setting a point at which a rise speed of the battery voltage of the secondary battery slows down as a lithium plating occurrence point and charging limitation.

A secondary battery system according to the present disclosure is a secondary battery system including a secondary battery, and the secondary battery system includes a dV/dQ calculation means configured to calculate a value of dV/dQ, the value of dV/dQ being a ratio of a variation dQ of an amount of stored energy Q to a variation dV of battery voltage V of the secondary battery when the amount of stored energy Q in the secondary battery changed during charging of the secondary battery, wherein a point at which a slope increase slows down on a SOC-dV/dQ graph showing a relationship between SOC and dV/dQ is determined as a lithium plating occurrence point in a negative electrode of the secondary battery.

The secondary battery system may include a current sensor to sense a current value I flowing in the secondary battery; a voltage sensor to sense battery voltage of the secondary battery; and a controller as the dV/dQ calculation means, and the controller may estimate an amount of stored energy in the secondary battery by integrating the current value for each predetermined time, obtain the battery voltage for each predetermined time by synchronizing with the integrated current, and calculate a value of dV/dQ by differentiating the battery voltage of the secondary battery with respect to its corresponding amount of stored energy during charging of the secondary battery.

Here, the controller may stop charging when determining as the lithium plating occurrence point. Instead, the controller may reduce at least one of charge current and charge voltage to the secondary battery while being charged, to accomplish full charge, when determining as the lithium plating occurrence point.

Advantageous Effects

According to the present disclosure, lithium plating can be detected in real time in an actual use environment of a lithium ion secondary battery. This method is non-destructive and can detect not only in real time but also in an actual use environment, providing an effect on accurate determination of the state of a secondary battery.

The method for detecting lithium plating according to the present disclosure can be used to set a charging condition in which lithium plating does not occur. Using this, a secondary battery can be charged rapidly and degradation caused by lithium plating can be prevented, ensuring a long life.

Because care should be taken of lithium plating, especially when charging rapidly at a high charge rate, the present disclosure is useful in quick charging. In accordance with the apparatus and method for charging a secondary battery according to the present disclosure, a secondary battery is charged without lithium-plating, there is no side reaction of deposited lithium with an electrolyte solution and changes in kinetic balance of the secondary battery, and the cause of degradation of the secondary battery is prevented. Charging is accomplished at a high charge rate within the limitation that does not cause lithium-plating, thereby achieving fast charging.

Changes in battery voltage as a function of SOC may differ in each secondary battery. The present disclosure accurately grasps a condition in which lithium-plating occurs during charging based on testing of the secondary battery and proposes an optimum charging approach for each secondary battery, rather than uniform charging limitation proposal irrespective of the characteristics of the secondary battery.

The secondary battery system according to the present disclosure implements a method for detecting lithium plating. By this system, the state of the secondary battery can be accurately detected in a convenient manner while the secondary battery is being used, and there is an effect on impeding the propagation of degradation of the secondary battery by dealing with a situation such as lithium plating rapidly.

BRIEF DESCRIPTION OF DRAWINGS

The accompanying drawing illustrates a preferred embodiment of the present disclosure and together with the foregoing disclosure, serves to provide further understanding of the technical spirit of the present disclosure. However, the present disclosure is not construed as being limited to the drawing.

MODE FOR DISCLOSURE

Hereinafter, preferred embodiments of the present disclosure will be described in detail with reference to the accompanying drawings. However, the present disclosure is not limited to the embodiments disclosed below and will be embodied in a variety of different forms, and this embodiment is only provided to fully disclose the present disclosure, and give those skilled in the art a complete understanding of the scope of the invention.

First of all, the background of how the present disclosure was derived is described with reference to FIG. 1.

Figure 1:
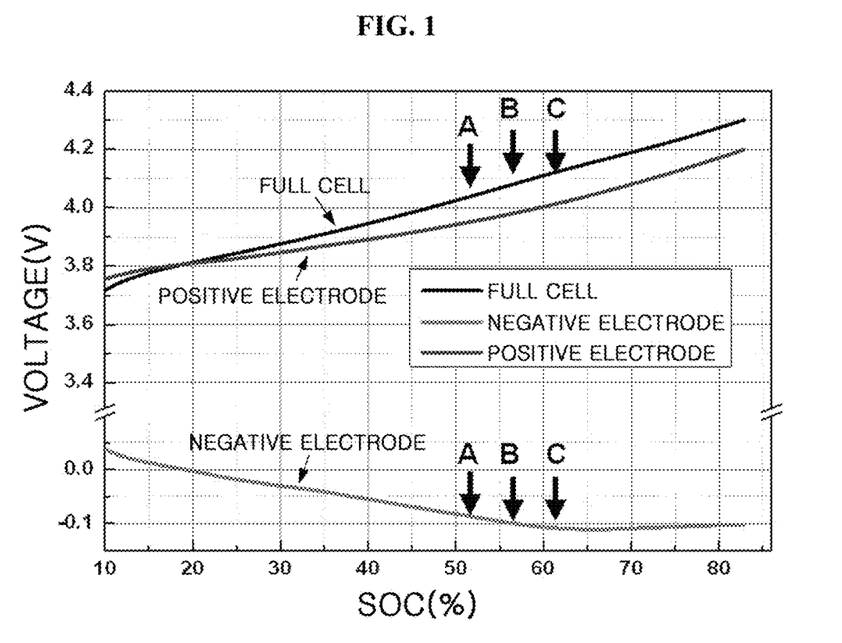
FIG. 1 is a potential vs SOC graph obtained by fabricating a $LiNi_xCo_yMn_zO_2$/graphite tri-electrode cell according to experimental example of the present disclosure and charging it at the charge rate of 3 C.

FIG. 1 is a potential vs SOC graph (SOC-V graph) by fabricating a $LiNi_xCo_yMn_zO_2$/graphite tri-electrode cell according to experimental example of the present disclosure and charging it at the charge rate of 3 C. As well know, a tri-electrode cell is used in the study of a secondary battery to investigate behaviors of each of a negative electrode and a positive electrode, and it has a unit cell and a reference electrode.

Generally, during charging, lithium intercalates into a negative electrode active material. and the lower the stage is, the lower the negative electrode potential is. In this instance, if the charge current density is increased, the stage is not observed well, but due to intercalation of lithium and resistance increases, the negative electrode potential continues its descent. It can be seen from FIG. 1 that the negative electrode potential continuously reduces to point A.

However, during charging, a reaction in which lithium intercalates into a negative electrode active material and a reaction in which lithium-plating occurs competitively occur. The inventors discovered through repeated experimentation that when lithium-plating occurs during charging, lithium does not intercalate into a negative electrode active material, causing changes in potential drop of a negative electrode. That is, they found that when lithium plating starts, the negative electrode reduces in the speed at which the potential drops. In FIG. 1, changes in drop speed are observed at point B of the negative electrode potential. Also, subsequent to point B, a region in which a predetermined flat plateau in the negative electrode potential appears is observed, and point C resides in such a region.

On the other hand, in the case of the positive electrode, the potential continues its rise during charging irrespective of lithium plating at the negative electrode. This can be also observed in the positive electrode potential of FIG. 1.

The battery voltage (full cell potential) is determined by a potential difference between the positive electrode and the negative electrode. Accordingly, the potential changes of the negative electrode as a result of lithium plating affect the battery voltage, and in FIG. 1, it can be seen that there are changes in battery voltage at points A, B, C.

In the case of a secondary battery, not a tri-electrode cell fabricated for experimentation, only the battery voltage can be measured in an actual use environment. Therefore, the inventors discovered that it is possible to detect lithium plating at the negative electrode in real time when observing changes in battery voltage during charging, and proposed the present disclosure.

The inventors determine point B in which changes in potential drop speed at the negative electrode are observed as shown in FIG. 1 as a lithium plating occurrence point, and by making use of the fact that changes in negative electrode potential are reflected on changes in battery voltage, propose a method for detecting lithium plating at the negative electrode in real time by observing changes in battery voltage as a parameter that can be measured in an actual use environment of a secondary battery. In this method, a point in which the battery voltage rise speed slows down as shown in point B of FIG. 1 is determined as a lithium plating occurrence point.

Figure 2:
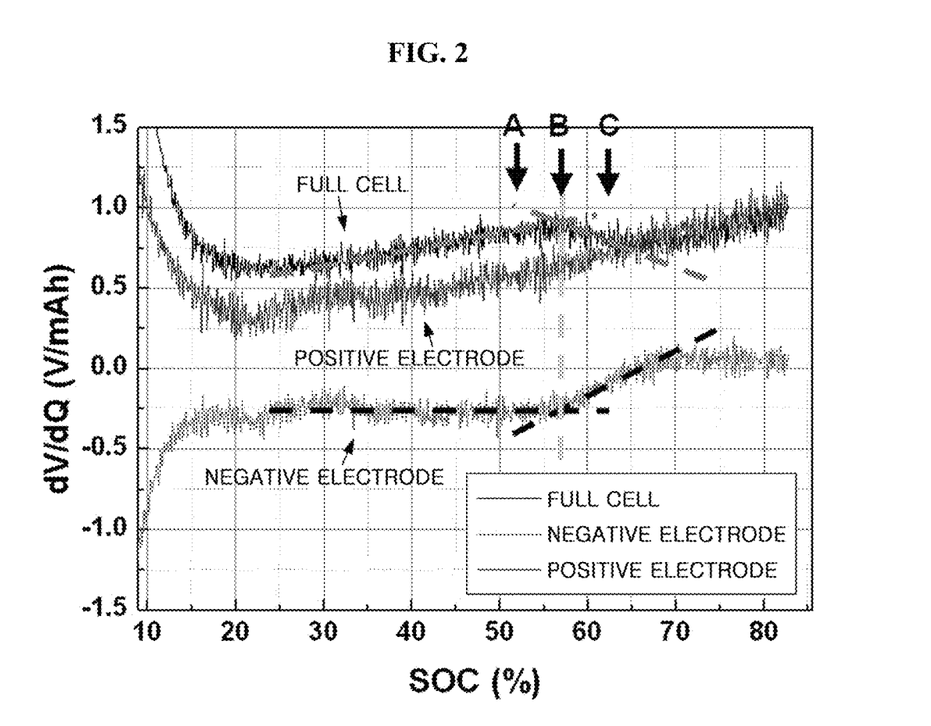
FIG. 2 is a change in potential with respect to a change in charge capacity (dV/dQ) vs SOC graph obtained from FIG. 1.

To find the point in which lithium-plating occurs more accurately, a SOC-dV/dQ graph showing a change in potential with respect to a change in charge capacity (dV/dQ) vs SOC can be plotted as shown in FIGS. 1 and 2.

Seeing dV/dQ of FIG. 2, in the case of the negative electrode potential, point B is an inflection point, and in the case of the battery voltage, the slope increase slows down at point B. The point B in which lithium plating at the negative electrode is determined to have occurred is created at a point in which the slope increase slows down on a change in potential with respect to a change in charge capacity (dV/dQ) vs SOC in an actual use environment of a secondary battery. Accordingly, it is suggested that a SOC-dV/dQ graph is obtained during charging of a secondary battery, and a point in which the slope increase slows down on dV/dQ is determined as a lithium plating occurrence point.

An experiment was conducted to verify the effectiveness of the method for detecting lithium plating. Three secondary batteries having the same unit cell as the tri-electrode cell used in the above experiment were prepared, one was charged and discharged to the point (point B in FIG. 2) in which lithium-plating is determined to occur, the other was charged and discharged before the lithium-plating occurrence point (up to point A), and another was charged and discharged after the lithium-plating occurrence point (up to point C) during charge and discharge cycles, and their results are shown in FIG. 3.

The life of a battery is a measure of how long a secondary battery can be used, and is indicated in number of cycles, and it is termed cycle characteristic. That is, the life of a battery refers to how many a secondary battery can be recharged, and in the sense of electrical energy, a period of time during which a secondary battery is used until it is fully discharged after charged once is a cycle, and the number of cycles is life.

Figure 3:
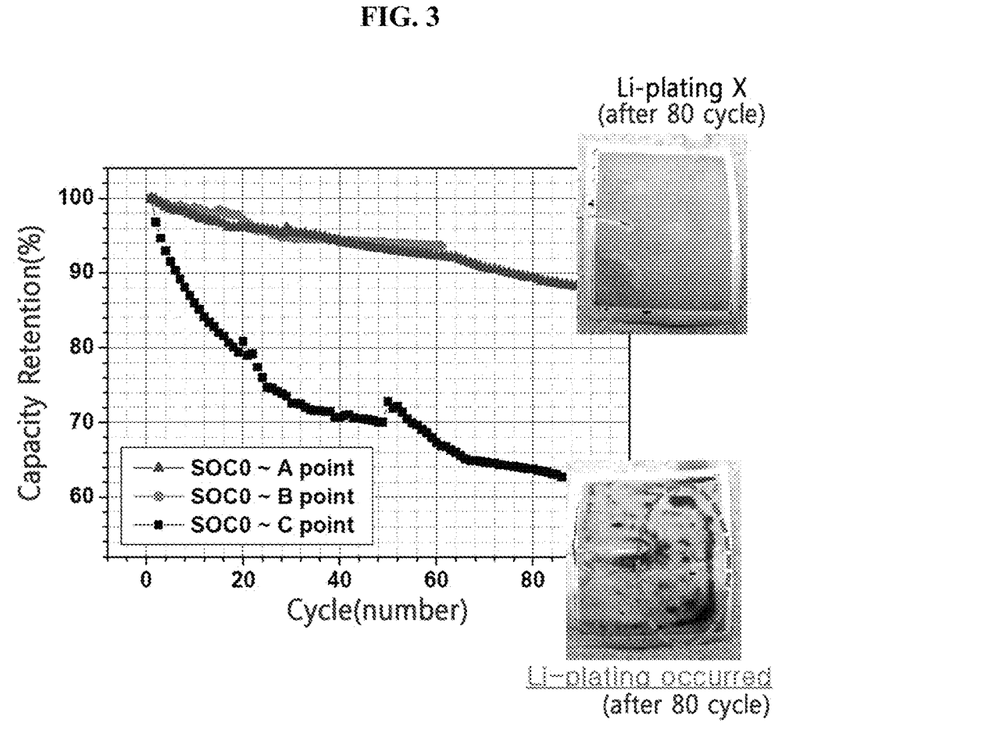
FIG. 3 is a cycle life comparison graph for verifying the effectiveness of a method for detecting lithium plating according to the present disclosure.

FIG. 3 shows changes in capacity as a function of the number of cycles. The condition was 30° C. 1.6 C charge and 0.33 C discharge. To have a long life, a secondary battery needs to maintain the capacity as original without significant reduction even for long charge and discharge cycles.

As can be seen from FIG. 3, after 80 cycle life test to point C, when a cell is dissembled, a great deal of lithium-plating is observed. In contrast, in the case of a cell charged and discharged for 80 cycles to points A and B, lithium-plating was not observed. Also, as can be seen from the life test results, a cell charged and discharged to point C reduced in capacity retention to 80% even after performing 20 cycles, and the capacity retention was below 64% after 80 cycles.

It can be seen that plated lithium generated during charging and discharging (as a result of lithium plating occurred during charging to point C) causes cell life characteristics to degrade. As proposed by the present disclosure, point B is determined as a lithium plating occurrence point, and when a cell is charged during cycles using it as a charging limitation, the capacity retention is maintained, and degradation of the cell is prevented, resulting in prolonged life.

As such, the method for detecting lithium plating according to the present disclosure can be used to set a charge protocol at the initial time of using a secondary battery by determining a lithium plating occurrence point using this method and setting it as a charging limitation, and when charged accordingly, a secondary battery can have a long life without lithium plating. Hereinafter, a method and apparatus for charging a secondary battery according to the present disclosure will be described in further detail.

Figure 4:
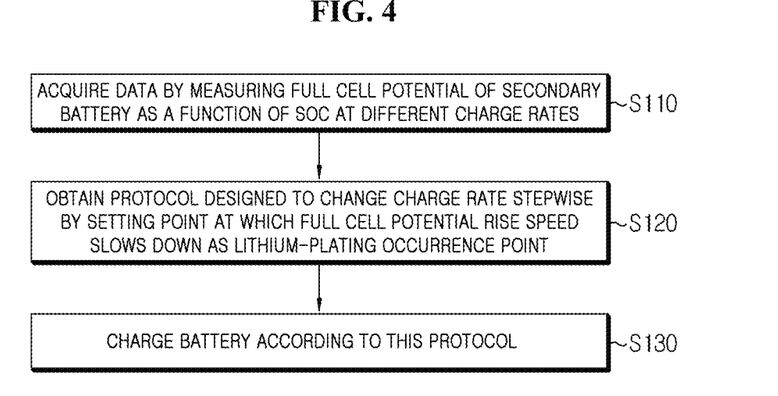
FIG. 4 is a flowchart of a method for charging a secondary battery according to the present disclosure.
Figure 5:
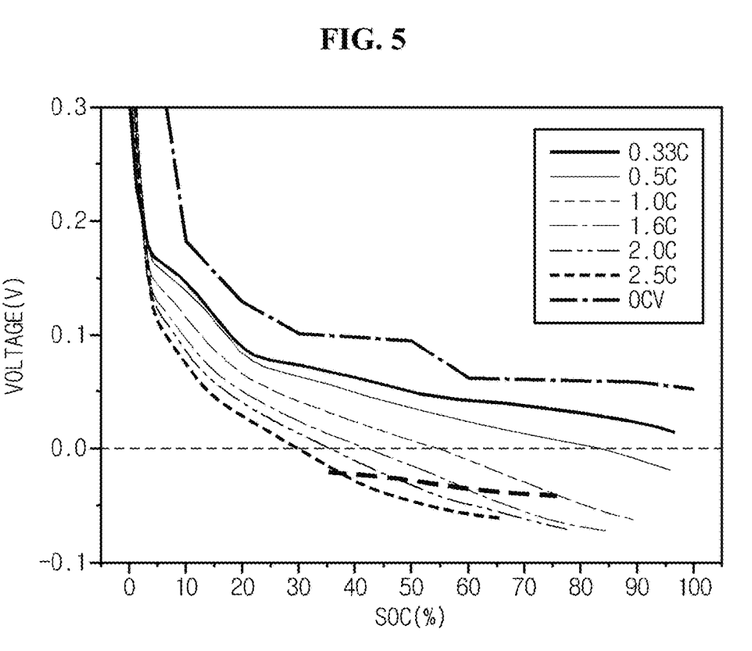
FIG. 5 is a battery voltage vs charge rate presented to describe a method for charging a secondary battery according to the present disclosure and battery voltage during protocol-oriented charging based on it.

A method for charging a secondary battery using the method for detecting lithium plating according to the present disclosure is first descried with reference to FIGS. 4 and 5.

FIG. 4 is a flowchart of a method for charging a secondary battery according to the present disclosure.

Referring to FIG. 4, a data acquisition step is performed in which the battery voltage of a secondary battery (full cell potential) as a function of SOC is measured at different charge rates (S110).

If "C" is secondary battery capacity of A·h in charge unit (often indicated as Q), an electric current in ampere unit is selected as a fraction (or a multiplier) of C. For example, 1 C charge rate refers to a charge/discharge rate at which the capacity of a fully charged secondary battery is consumed or replenished within one hour, and also may refer to a current density at the time. Recently, with diverse functions of electronic devices, an amount of current required for use in devices within a predetermined period of time increases in a high proportion. Accordingly, a secondary battery used as an energy source is required to have much higher performance. In the case of mobile phones, most of traditional mobile phones needed a charge and discharge rate of C/2, but as these functions improve in the future, performance corresponding to a charge and discharge rate of 1 C will be required. Currently, secondary batteries for laptop computers, EV, and PHEV require a similar charge rate and a much higher discharge rate.

The charge rate higher than 1C is desirable from the point of view of fast charging. However, if a secondary battery is continuously charged with high current, high heat generation may occur inside the secondary battery, and due to resistance of the secondary battery, each electrode may be in overvoltage state. Accordingly, the charge rate should be set in consideration of the type and characteristics of secondary battery.

The range of charge rate in the data acquisition step may change depending on the type and characteristics of secondary battery. For example, secondary batteries for EV set an initial charge rate to 1.5 C and acquire data in the range of charge rate of 0.25 C~1.5 C. As another example, secondary batteries for plug-in hybrid electric vehicle (PHEV) set an initial charge rate to 3 C and acquire data in the range of charge rate of 0.25 C~3 C. The range of initial charge rate and charge rate may be limited by not only the type of secondary battery but also a maximum current of a motor actually used in vehicle.

As previously mentioned, in consideration of characteristics of secondary battery, secondary batteries for EV may have an initial charge rate set to 1.5 C, and secondary batteries for PHEV may have an initial charge rate set to 3 C. According to the secondary battery specification needed for a higher charge rate and a higher discharge rate, the initial charge rate may be increased, for example, up to 5 C. Accordingly, the initial charge rate may be from 1.5 C to 5 C, and the range of charge rate at the data acquisition step of the present disclosure may be in the range of 0.25 C~5 C.

As previously mentioned, deeper interest and more intensive studies concentrate on secondary batteries for vehicle as a key component of HEV or EV, and along with this, there is an urgent need for the development of fast charging technology to charge secondary batteries rapidly. The demand for charge time is gradually increasing in the automobile market, and to meet the demand, a higher initial charge rate is needed. From the viewpoint of fast charging, a high initial charge rate is advantageous, but due to the problem as discussed previously, there is concern that each electrode will become an overvoltage state at a too high charge rate due to the resistance of secondary batteries. Also, at too high charge rate, charging reaches the limitation at the same time as the start, so the total charge time may be not significantly reduced. Thus, to increase the initial charge rate, improvements in resistance characteristics of secondary batteries should be involved together. The present disclosure can increase the initial charge rate up to 5 C for secondary batteries with improved resistance as compared to traditional secondary batteries.

FIG. 5 shows battery voltage vs charge rate. As shown in FIG. 5, a graph can be obtained by measuring battery voltage as a function of SOC, with varying charge rates from 2.5 C to 0.33 C.

Subsequently. from the acquired data, by setting a point at which the battery voltage rise speed slows down as a lithium-plating occurrence point, protocol designed to change a charge rate stepwise is obtained (S120). If the point at which the battery voltage rise speed slows down is set as the lithium-plating occurrence point, the secondary battery can be charged without causing lithium-plating to the negative electrode.

For example, in FIG. 5, if the point at which the battery voltage rise speed slows down is set as the lithium-plating occurrence point and the charging limitation, protocol such as Table 1 can be obtained.

TABLE 1

| C-rate | SOC | Delta SOC | Charge time (min) |
|---|---|---|---|
| 2.5 | 33 | 27 | 6.48 |
| 2 | 45 | 12 | 3.6 |
| 1.6 | 58 | 13 | 4.875 |
| 1 | 73 | 15 | 9 |
| 0.5 | 78 | 5 | 6 |
| | | | 29.955 |

Referring to Table 1 and FIG. 5 together, in charging at the initial charge rate of 2.5 C, lithium-plating occurs at a point at which SOC is 33% (a point at which a solid line indicating the potential 0V and a potential graph meet). Subsequently, the charge rate is changed to the next charge rate 2 C. In charging accordingly, lithium-plating occurs at the point at which SOC is 45%. Thus, the charge rate is changed to the next charge rate 1.6 C. In charging accordingly, lithium-plating occurs at the point at which SOC is 58%. Thus, the charge rate is changed to the next charge rate 1 C. In charging accordingly, lithium-plating occurs at the point at which SOC is 73%. Thus, the charge rate is changed to the next charge rate 0.5 C. In charging accordingly, lithium-plating occurs at the point at which SOC is 78%. Using this stepwise reduction in charge current, the time taken to charge until SOC reaches 78% is 29.955 minutes in total.

As seen from Table 1, a large SOC variation can be obtained at a high charge rate in the initial time. and accordingly, the total charge time can be shortened, and especially, even in the case of rapid charging, the charge rate is not maintained at high condition all the time and is changed stepwise in consideration of lithium plating, thereby producing an effect on charging without a lithium plating problem.

Through the method described above, an effective charge protocol can be obtained for each secondary battery. Although the battery voltage vs SOC graph changes according to the type of secondary battery, this method by which the protocol is obtained is equally applied.

Also, although this embodiment describes that the charge rate is reduced from 2.5 C to 0.5 C, the range of initial charge rate and the range of charge rate at the data acquisition step may change as mentioned previously, and an amount of reduction of the charge rate may be an arbitrary value, not 0.5 C, 0.6 C, 0.4 C as in this embodiment.

Subsequently, after this protocol is obtained, the secondary battery is charged (S130). The protocol may include the stepwise-decreasing charge rate and charge voltage information after termination of charging at each charge rate. If secondary batteries are charged according to this charge protocol, the secondary batteries can be charged rapidly without a lithium plating problem. As such, according to the present disclosure, a charge protocol can be obtained under the condition in which lithium plating does not occur, and according to this protocol, fast charging can be achieved by applying an optimized charge current.

The charge protocol may be realized using an apparatus for charging a secondary battery according to the present disclosure as described below.

Figure 6:
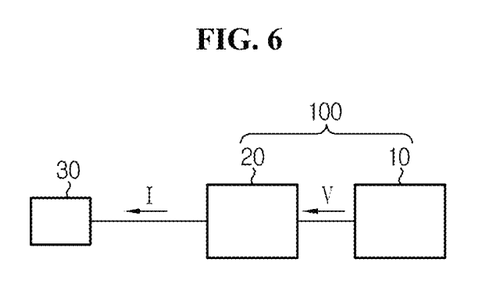
FIG. 6 is an outline diagram of an apparatus for charging a secondary battery according to the present disclosure.

FIG. 6 is an outline diagram of an apparatus for charging a secondary battery according to the present disclosure.

Referring to FIG. 6, the apparatus 100 for charging a secondary battery includes a power source unit 10 and a charging unit 20.

The power source unit 10 outputs charge voltage inputted from a commercial power source.

The charging unit 20 outputs the charge voltage inputted from the power source unit 10 to a secondary battery 30 as a charge current, to charge the secondary battery 30. In this instance, if the charge voltage (battery voltage) of the secondary battery 30 reaches a preset stage, the charging unit 20 takes control of the charge current to cause the charge current outputted to the secondary battery 30 to change stepwise.

Particularly, the charging unit 20 charges the secondary battery with the stepwise-adjusted charge current according to the protocol designed to change the charge rate stepwise by setting a point at which the battery voltage rise speed of the secondary battery 30 slows down as a lithium-plating occurrence point. The logic of the protocol of the charging method according to the present disclosure may be incorporated into the apparatus 100 for charging a secondary battery and used to charge the secondary battery 30.

The charging unit 20 employs a processor for embodying fast charging. According to the embodiment of the present disclosure, the processor stores logic of the charge protocol in memory, and can enable precise control over voltage and current and measure voltage and current with high accuracy to ensure the apparatus performance.

In accordance with the method and apparatus for charging a secondary battery according to the present disclosure, because it has a charging process controlling to avoid going the lithium-plating occurrence point during charging, when compared to a general charging scheme. there is no concern that lithium-plating will occur to the negative electrode, and accordingly, there is an effect on longer life of the secondary battery.

Figure 7:
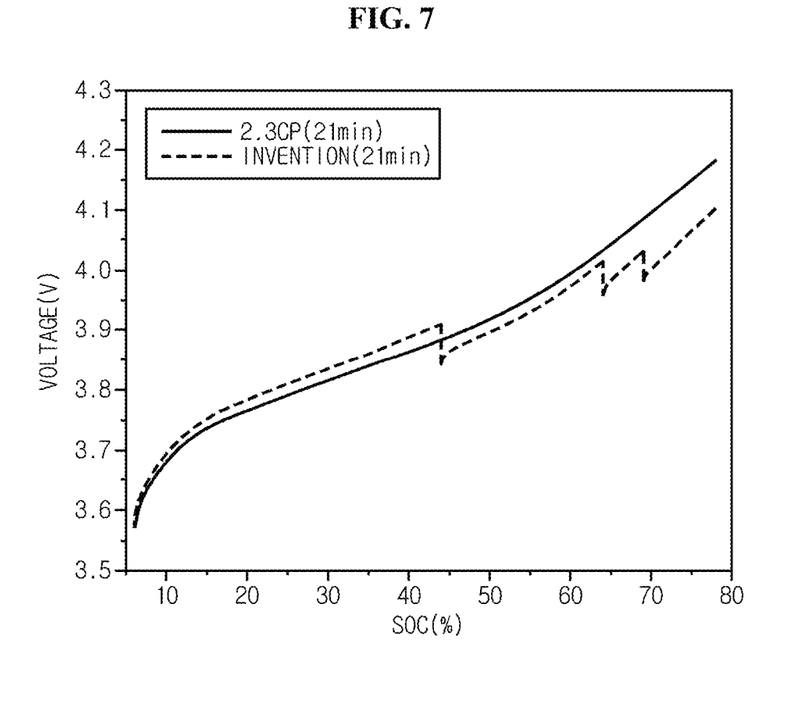
FIG. 7 is a battery voltage vs SOC graph for a charging method using a stepwise reduction in charge current according to the present disclosure and a conventional CP charging scheme.
Figure 8:
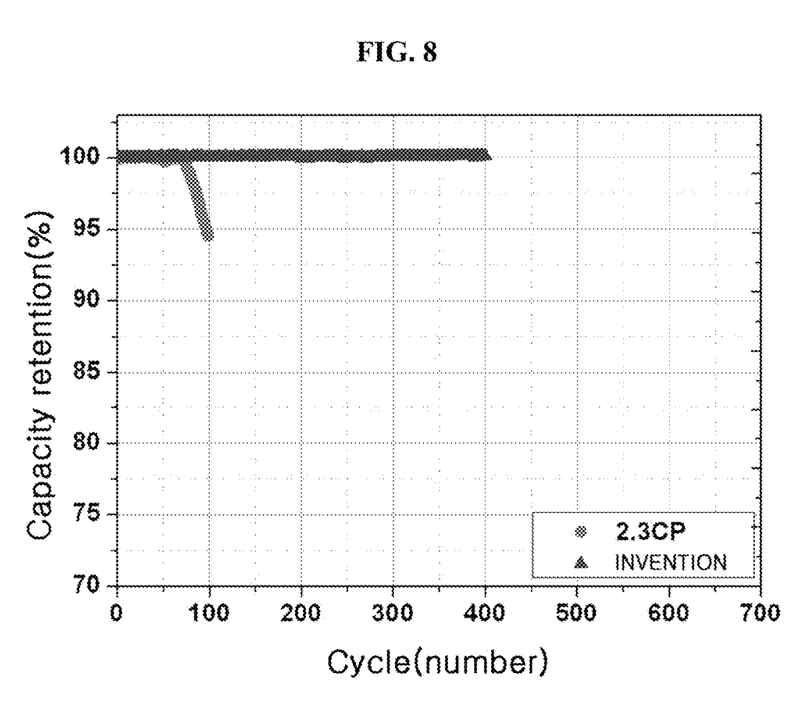
FIG. 8 is a graph comparing the life of a secondary battery between a charging method using a stepwise reduction in charge current according to the present disclosure and a conventional CP charging scheme.

FIGS. 7 and 8 are a SOC-battery voltage graph and a life comparison graph comparing the charging method using a stepwise reduction in charge current according to the present disclosure and a conventional CP (constant power) charging scheme.

Table 2 is the charge protocol according to the present disclosure used in experimentation. A 10-second rest was given between each charging stage.

TABLE 2

| C-rate | SOC | Delta SOC | Charge time (min) | Rest (sec) |
|---|---|---|---|---|
| 2.59 | 44 | 38 | 8.80 | 10 |
| 2.07 | 64 | 20 | 5.80 | 10 |
| 1.66 | 69 | 5 | 1.81 | 10 |
| 1.24 | 78 | 9 | 4.35 | |
| | | | 21 min | |

FIG. 7 shows the battery voltage as a result of charging. In the present disclosure and the conventional art, the charge time was 21 minutes equally. The conventional art (CP) tends to show a continuous rise in voltage, while the charging method according to the present disclosure shows a saw-like rising curve due to changes between each charging stage because it uses a stepwise reduction in charge current.

FIG. 8 is a graph comparing the life of the secondary battery between the charging method using a stepwise reduction in charge current according to the present disclosure and the conventional CP charging scheme. In the present disclosure and the conventional art, the life of each case was compared where the charge time was 21 minutes equally and discharging was performed under the same condition (1 C CC).

In the conventional art (CP) as shown in FIG. 8, the capacity retention starts to reduce after 75 cycles, and after 100 cycles, the capacity retention reduces to about 95%, while in the case of the present disclosure (step charge), the capacity retention amounts to 100% even after 400 cycle.

The life of the secondary battery is set by various factors, and structural stability of the electrode, especially, stability of the negative electrode, is important. An ideal negative electrode should have high reaction reversibility with lithium ions. If an ideal reversible reaction is accomplished, there is no change in capacity retention based on cycle. It can be seen that the charging method using a stepwise reduction in charge current according to the present disclosure has higher reaction reversibility than the conventional art, and it is a result of preventing lithium-plating at the negative electrode. As such, in accordance with the charging method using a stepwise reduction in charge current according to the present disclosure, it can be seen that the secondary battery has a longer life than the conventional art by preventing degradation.

The charging method using a stepwise reduction in charge current according to the present disclosure charges the secondary battery rapidly using the initial charge rate higher than 1 C with a stepwise decrease in charge rate by setting the point at which the battery voltage rise speed slows down as the lithium-plating occurrence point, thereby charging the secondary battery rapidly without lithium-plating occurrence. Damage to the internal structure of the secondary battery can be prevented, and the life of the secondary battery can be improved.

Also, the method for detecting lithium plating according to the present disclosure can be used to monitor the state of the secondary battery in using the secondary battery, and stop charging or change the charge protocol in response to lithium plating detected. This is a secondary battery system using the method for detecting lithium plating according to the present disclosure.

Figure 9:
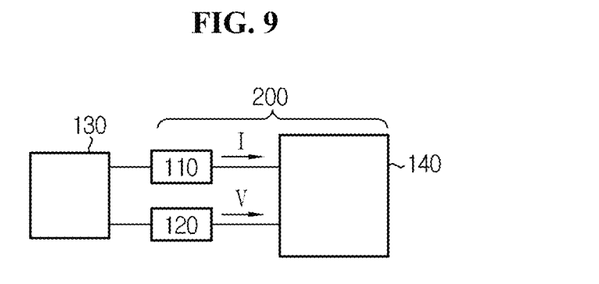
FIG. 9 is an outline diagram of a secondary battery system according to the present disclosure.

FIG. 9 is an outline diagram of the secondary battery system according to the present disclosure.

The method for detecting lithium plating according to the present disclosure may be embodied as the secondary battery system 200 as shown in FIG. 9. Generally, the secondary battery system detects the state of a secondary battery such as a state of charge (remaining capacity or SOC) based on the voltage of the secondary battery, and the secondary battery system 200 according to the present disclosure is characterized in that it can detect lithium plating.

Referring to FIG. 9, the secondary battery system 200 includes a secondary battery 130, a current sensor 110, a voltage sensor 120, and a controller 140. The controller 140 employs a processor having a memory such as ROM and RAM.

The current sensor 110 senses a current value I flowing in the secondary battery 130. Also, the voltage sensor 120 senses the battery voltage V (voltage across terminals) of the secondary battery 130, i.e., full cell potential. The current value I and the battery voltage V is converted to digital data, for example, by an A/D converter and the processor of the controller 140 can obtain the data.

The controller 140 calculates an amount of charged energy or discharged energy of the secondary battery 130 by integrating the current value I sensed by the current sensor 110 for each predetermined time t, and estimates an amount of stored energy Q of the secondary battery 130 from the calculated amount of charged energy or discharged energy. Also, the controller 140 acquires the battery voltage V of each secondary battery 130 sensed by the voltage sensor 120 for each predetermined time t by synchronizing with the integrated current.

Also, the controller 140 calculates a value of dV/dQ, namely, a ratio of a variation dQ of the amount of stored energy Q to a variation dV of the battery voltage V of the secondary battery 130 when the amount of stored energy Q of the secondary battery 130 changed. Particularly, during charging of the secondary battery 130, a value of dV/dQ is calculated by differentiating battery voltage V of the secondary battery 130 with respect to its corresponding amount of stored energy Q.

Specifically, during charging of the secondary battery 130, battery voltage V and an amount of stored energy Q is acquired for each predetermined time t, and a variation dV of the battery voltage V and a variation dQ of the amount of stored energy Q are calculated for each predetermined time t, and based on them, a value of dV/dQ is calculated for each predetermined time t.

As described in the foregoing, the dV/dQ value is continuously monitored for each predetermined time t, and when a point at which the slope increase slows down takes place on dV/dQ, the controller 140 determines it as a lithium plating occurrence point. That is, the method for detecting lithium plating according to the present disclosure is performed by the controller 140, and the controller 140 determines whether plating occurred by detecting whether lithium plating occurs in the secondary battery 130.

When the controller 140 determines that lithium plating occurred, the controller 140 may stop charging or change the charge condition to accomplish full charge (for example, up to SOC 80%). In the case of changing the charge condition, it may be accomplished by reducing at least one of charge current and charge voltage to the secondary battery 130 while being charged. The secondary battery system 200 may be configured to stop charging and change the charging condition through a control command for a charge/discharge circuit (not shown) of the secondary battery 130. For example, an I/O interface may be included the processor of the controller 140 to allow the controller 140 to control the charge/discharge circuit through it.

Hereinabove, while the preferred embodiments of the present disclosure have been illustrated and described, the present disclosure is not limited to the particular preferred embodiment described above, and it is apparent to those skilled in the art that modifications may be made in various forms without departing from the features of the present disclosure set forth in the claims, and such modifications reside in the scope of the claims.

What is claimed is:

1. A method for detecting lithium plating of a secondary battery and controlling the secondary battery, the method comprising:

for each of a plurality of charge rates, detecting lithium plating in a negative electrode of the secondary battery by determining a change in voltage of the secondary battery as a function of a state of charge (SOC) during charging of the secondary battery;

for each charge rate, determining a point at which a rise speed of the battery voltage slows down as a lithium plating occurrence point;

for each charge rate, setting the lithium plating occurrence point as a charging limitation; and charging the secondary battery according to the respective charging limitations, wherein charge rate of the secondary battery is reduced stepwise.

2. The method for detecting lithium plating according to claim 1, wherein the method comprises:

obtaining a SOC-V graph by measuring battery voltage as a function of SOC while charging the secondary battery;

obtaining a SOC-dV/dQ graph showing a change in battery voltage dV/dQ as a function of SOC from the SOC-V graph; and determining a point at which a slope increase slows down on the SOC-dV/dQ graph as the lithium plating occurrence point.

3. A method for charging a secondary battery, comprising:

acquiring data by measuring battery voltage as a function of SOC at different charge rates;

at each charge rate, determining a point at which a rise speed of the battery voltage slows down as a lithium plating occurrence point in a negative electrode of the secondary battery;

obtaining a protocol designed to reduce a charge rate stepwise limited by the lithium plating occurrence point at the respective charge rate; and charging the secondary battery according to the protocol.

4. The method for charging a secondary battery according to claim 3, wherein the charge rate at the data acquisition step is in a range of 0.25 C~5 C.

5. The method for charging a secondary battery according to claim 3, wherein the protocol has an initial charge rate higher than 1 C.

6. The method for charging a secondary battery according to claim 3, wherein the protocol has an initial charge rate of from 1.5 C to 5 C.

7. The method for charging a secondary battery according to claim 3, wherein the protocol includes charge voltage information after termination of charging at each charge rate.

8. An apparatus for charging a secondary battery, comprising:

a power source unit configured to output charge voltage inputted from a commercial power source;

a charging unit configured to output the charge voltage inputted from the power source unit to a secondary battery as a charge current, to charge the secondary battery, and when battery voltage of the secondary battery reaches a preset stage, to take control of the charge current to cause the charge current outputted to the secondary battery to reduce stepwise; and a controller configured to at each charge current, determine a point at which a rise speed of the battery voltage slows down as a lithium plating occurrence point in a negative electrode of the secondary battery, wherein the charging unit charges the secondary battery with the stepwise-adjusted charge current according to a protocol designed to reduce a charge rate limited by the lithium plating occurrence point at the respective charge current.

9. A secondary battery system, comprising a secondary battery and a controller, wherein the controller is configured to:
- calculate a value of dV/dQ of the secondary battery, the value of dV/dQ being a ratio of a variation dQ of an amount of stored energy Q to a variation dV of battery voltage V of the secondary battery when the amount of stored energy Q in the secondary battery changed during charging of the secondary battery,
- for a plurality of charge rates, determine a point at which a slope increase slows down on a SOC-dV/dQ graph showing a relationship between SOC and dV/dQ as the respective lithium plating occurrence point in a negative electrode of the secondary battery,
- for each charge rate, set the lithium plating occurrence point as a charging limitation, and
- charge the secondary battery using the plurality of charge rates limited to their respective charging limitation, wherein the charging rate is reduced stepwise.

10. The secondary battery system according to claim 9, wherein the secondary battery system comprises:
- a current sensor to sense a current value I flowing in the secondary battery; and
- a voltage sensor to sense battery voltage of the secondary battery;
- wherein the controller estimates an amount of stored energy in the secondary battery by integrating the current value for each predetermined time, obtains the battery voltage for each predetermined time by synchronizing with the integrated current, and calculates a value of dV/dQ by differentiating the battery voltage of the secondary battery with respect to its corresponding amount of stored energy during charging of the secondary battery.

11. The secondary battery system according to claim 9, wherein the controller stops charging when determining as the lithium plating occurrence point.

12. The secondary battery system according to claim 9, wherein the controller reduces at least one of charge current and charge voltage to the secondary battery while being charged, to accomplish full charge, when determining as the lithium plating occurrence point.

* * * * *